(12) United States Patent
Choi et al.

(10) Patent No.: US 8,580,291 B2
(45) Date of Patent: Nov. 12, 2013

(54) FIBROUS COMPOSITE FOR TISSUE ENGINEERING

(75) Inventors: Hoon Choi, Bryn Mawr, PA (US); I. Wei Chen, Swarthmore, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 2052 days.

(21) Appl. No.: 10/507,059

(22) PCT Filed: Mar. 14, 2003

(86) PCT No.: PCT/US03/08128
§ 371 (c)(1),
(2), (4) Date: Sep. 9, 2004

(87) PCT Pub. No.: WO2005/007802
PCT Pub. Date: Jan. 27, 2005

(65) Prior Publication Data
US 2005/0226904 A1    Oct. 13, 2005

Related U.S. Application Data

(60) Provisional application No. 60/364,876, filed on Mar. 15, 2002.

(51) Int. Cl.
*A61K 9/70* (2006.01)
*A61F 2/00* (2006.01)

(52) U.S. Cl.
USPC ........... 424/426; 424/443; 424/617; 424/724; 514/492; 514/772.3; 514/772.6; 514/773

(58) Field of Classification Search
None
See application file for complete search history.

(56) References Cited

U.S. PATENT DOCUMENTS

| 4,171,544 | A | | 10/1979 | Hench et al. |
| 4,394,370 | A | | 7/1983 | Jefferies |
| 4,472,840 | A | | 9/1984 | Jefferies |
| 4,748,121 | A | * | 5/1988 | Beaver et al. ................. 435/176 |

(Continued)

FOREIGN PATENT DOCUMENTS

WO    WO 9745367 A1 * 12/1997
WO    WO 9853768 A1 * 12/1998

OTHER PUBLICATIONS

Shvets et al, Characteristics of Template Formation in Silica in Acidic Media, Theoretical anbd Experimental Chemistry, vol. 37, No. 2, 2001, 112-115.*

(Continued)

*Primary Examiner* — Ernst Arnold
*Assistant Examiner* — Jianfeng Song
(74) *Attorney, Agent, or Firm* — RatnerPrestia

(57) ABSTRACT

Provided are fibrous composites prepared by methods of the present invention, comprising oxides and biodegradable polymers, in which the fibers are made of aerogel-like oxide materials having nanometer-sized pores. The fibrous composition advantageously has, at least, the following characteristics: (i) a very high nanoporous surface area, which also permits nucleation of crystallites; (ii) mesoporous/macroporous interspacial networks between the fibers, providing high bioactivity and a high transport rate; (iii) macropores for natural bone-like tissue growth; (iv) good mechanical properties for handling and for implant support; and (v) biodegradability for implant dissolution and time-variable mechanical properties. Further provided are methods for using the bioactive biodegradable fibrous composites as osteogenic composite materials for tissue engineering, tissue re-growth, bone implants, and bone repair, and/or for the delivery of drugs or therapeutic compounds.

15 Claims, 6 Drawing Sheets

(56) References Cited

U.S. PATENT DOCUMENTS

| | | | |
|---|---|---|---|
| 4,775,646 A | 10/1988 | Hench et al. | |
| 5,074,916 A | 12/1991 | Hench et al. | |
| 5,612,049 A * | 3/1997 | Li et al. | 424/422 |
| 6,261,679 B1 | 7/2001 | Chen et al. | |
| 6,302,913 B1 | 10/2001 | Ripamonti et al. | |
| 6,311,690 B1 | 11/2001 | Jefferies | |
| 6,328,990 B1 | 12/2001 | Ducheyne et al. | |
| 6,334,988 B1 | 1/2002 | Gallis et al. | |
| 6,482,444 B1 * | 11/2002 | Bellantone et al. | 424/618 |
| 2003/0021820 A1 * | 1/2003 | Ahola et al. | 424/422 |
| 2004/0009598 A1 * | 1/2004 | Hench et al. | 435/375 |

OTHER PUBLICATIONS

Schacht et al, Oil-Water Interface Templating of Mesoporous Macroscale Structures, Science, vol. 273, Aug. 9, 1996, 768-771.*

Wikipedia, Self-Assembly, Acquired online on Dec. 22, 2009.*

Gross, U et al., "Surface Activities of Bioactive Glass, Aluminum Oxide, and Titanium in a Living Environment," *Annals NY Academy of Science* (ed. Ducheyne and Lemons), 523: 211-226 (1988).

Hench, Larry L., "Bioactive Ceramics," *Annals NY Academy of Sciences* (ed. Ducheyne and Lemons), 523: 54-71 (1988).

Hench, Larry L. et al., "The Sol-Gel Process," *Chem. Rev.*, 90: 33-72 (1990).

Huo, Qisheng et al., "Mesostructure Design with Gemini Surfactants: Supercage Formation in a Three-Dimensional Hexagonal Array," *Science*, 268: 1324 (1995).

Kresge, C.T. et al., "Ordered Mesoporous Molecular Sieves Synthesized by a Liquid-Crystal Template Mechanism," *Nature*, 359: 710-712 (1992).

Kokubo, T. et al., "Solutions Able to Reproduce In Vivo Surface-Structure Changes in Bioactive Glass-Ceramic A-W$^3$," *J. of Biomedical Materials Research*, 24:721-734 (1990).

Li, P. et al., "The Bone-Bonding Polymer Polyactive 80/20 Induces Hydroxycarbonate Apatite Formation In Vitro," *J. of Biomedical Materials Research*, 34: 79-86 (1997).

Ogino, Makato et al., "Compositional Dependence of the Formation of Calcium Phosphate Films on Bioglass," *J. of Biomedical Materials Research*, 14: 55-64 (1980).

Qi, Limin et al., "Micrometer-Sized Mesoporous Silica Spheres Grown Under Static Conditions," *Chem. Mater.*, 10: 1623-1626 (1998).

Qiu, Q. et al., "Formation and Differentiation of Three-Dimensional Rat Marrow Stromal Cell Culture on Microcarriers in a Rotating-Wall Vessel," *Tissue Engineering*, 4(1): 19-34(1998).

Qiu, Qing-Qing et al., "Fabrication, Characterization and Evaluation of Bioceramic Hollow Microspheres Used As Microcarriers for 3-D Bone Tissue Formation in Rotating Bioreactors," *Biomaterials*, 20: 989-1001(1999).

Radin, S.R. et al., "The Effect of Calcium Phosphate Ceramic Composition and Structure on In Vitro Behavior. II. Precipitation," *J. of Biomedical Materials Research*, 27: 35-45(1993).

Schacht, S. et al., "Oil-Water Interface Templating of Mesoporous Macroscale Structures," *Science*, 273(5276): 768-771(1996).

Yang, Hong et al., "Synthesis of Mesoporous Silica Spheres Under Quiescent Aqueous Acidic Conditions," *J. of Materials Chemistry*, 8(3): 743-750(1998).

* cited by examiner (A)

(B)

(A)

(B)

(A)

(B)

(A)

(B)

FIBROUS COMPOSITE FOR TISSUE ENGINEERING

REFERENCE TO RELATED APPLICATION

This application claims priority to U.S. Provisional Application No. 60/364,876, filed Mar. 15, 2002, the content of which is herein incorporated by reference.

GOVERNMENT INTEREST

This invention was supported in part by U.S. National Science Foundation, Grant Number DMR00-79909. Accordingly, the Government may have certain rights in this invention.

FIELD OF THE INVENTION

The present invention relates to bioactive, biodegradable fibrous composite materials and their preparation and use, and more particularly to fibrous composite materials comprising oxides and biodegradable polymers, for use in tissue engineering, bone implants, and bone repair, as well as for drug or gene delivery devices.

BACKGROUND OF THE INVENTION

Conventional treatment of bone defects requires the use of either non-resorbable or resorbable prosthetic structures. The resorbable structures or materials either support the in growth of adjacent bone and soft tissue or actively induce the formation of new bone. The active formation of new bone, termed osteoinduction, occurs only in the presence of demineralized bone matrix or in the presence of protein extracts from such matrix (biomaterials), or a combination of both materials, preferably with interconnected porous spaces across the substratum of the biomaterial. This allows bone growth into the porous spaces of the biomaterial, securing its incorporation and osteointegration with the surrounding viable bone at the margins of the bone defect. Such porous biomaterials, which allow bone growth into their porous spaces, are defined as osteoconductive biomaterials.

The necessity of having viable bone in direct contact with the porous biomaterial to ensure adequate bone ingrowth via osteoconduction is, however, a limiting factor particularly in large bony defects, since the depth of bone penetration within the porous spaces may be confined to the peripheral regions of the implant only. Thus, osteointegration often does not occur or is not maintained along the entire implant surface. One approach for preparing an osteoinductive material has been to adsorb onto its surfaces exogenous growth and morphogenetic factors (collectively, bone morphogenetic proteins (BMPs)), which are capable of inducing differentiation of bone within the porous spaces of the biomaterial. See e.g., Jefferies et al., in U.S. Pat. Nos. 4,394,370; 4,472,840; 6,311,690 describing bone graft materials comprising collagen and demineralized bone matrix or extracted BMP. However, BMPs have limited shelf life and risk of adverse systemic effects. Therefore, a preferred alternative would be a bioactive material, which is capable of spontaneously initiating bone formation within the porous spaces independent of the presence of viable bone at its interfaces.

"Bioactivity" is a unique property associated with the ability of a synthetic material to interact or bond with living tissue. All materials implanted in vivo elicit a response from the surrounding tissue. Four types of response are possible: (i) tissue death if the material is toxic; (ii) replacement by the surrounding tissue if the material is nontoxic and dissolves; (iii) formation of a fibrous tissue capsule of variable thickness if the material is nontoxic and biologically inactive; and (iv) formation of an interfacial bone if the material is nontoxic and biologically active. Bioactive materials fall into the fourth category.

Hydroxyapatite is the most recognized bioactive material for bone tissue. The presence and formation of calcium hydroxyapatite at the implant-bone interface appears to be critical for bone bonding, and it is one of the key features necessary for successful bioactive bone implants. Calcium hydroxyapatite coatings on implants or calcium hydroxyapatite blocks have been used to produce implants with bone-binding abilities, e.g., U.S. Pat. No. 6,302,913 (Ripamonti) introduced the concept that the shape and configuration of the hydroxyapatite implant regulates the initiation of bone formation in vivo.

Moreover, it has been shown that several crystalline and amorphous (glassy) oxide materials can induce the growth of hydroxyapatite in the environment of simulated body fluid. Among them is silica ($SiO_2$), but several other oxides, such as $TiO_2$, $ZrO_2$ and $Ta_2O_5$, and various silica-based glasses are also effective. For example, through the use of an in vitro immersion method using a simulated physiological solution that mimics the ion concentration found in body fluids, the formation of the calcium hydroxyapatite layers on bioactive glasses, bioactive glass-ceramics and polymers have been produced. As a result, this method of "in vitro immersion" has been used to predict bone-bonding potential of bone implant materials (Kokubo et al., *J. Biomed. Mater. Res.* 24:721-734 (1990); Li et al., *J. Biomed. Mater. Res.* 34:79-86 (1997)). Therefore, these materials can also be regarded as bioactive. For example, at high pH, on the $SiO_2$ surface, the glass-solution interface is crystallized into a mixed hydroxyapatite phase of the CaO and $P_2CO_5$ that is released into solution during the network dissolution. Then, the hydroxyapatite crystallites nucleate and bond to the interfacial biological metabolites, such as mucopolysaccharides, collagen and glycoproteins.

Currently, bioactive powders are produced by conventional processing techniques well-known in the art. The various constituents (e.g., reagent-grade $Na_2CO_3$, $CaCO_3$, $P_2CO_5$ and $SiO_3$) are usually mixed in a suitable mixing device such as a rolling nill, and then heated to a temperature (generally 1250-1400° C.) sufficient to cause the particles to melt and coalesce. See, e.g., U.S. Pat. No. 4,775,646; Ogino et al., *J. Biomed. Mat. Res.* 14:55-56 (1980). However, the use of such high temperatures and specialized equipment results in significant production costs. Moreover, conventional bioactive glass compositions tend to require an alkali metal oxide such as $Na_2O$ to serve as a flux or aid in melting or homogenization, resulting in a high pH at the interface between the glass and surrounding fluid or tissue. Unfortunately in vivo, this can induce inflammation. Moreover, the rate of tissue repair, which drives the interfacial tissue-glass bonding promoted by bioactive material, tends to vary within a narrow pH range, and if the surrounding environment is too acidic or alkaline, repair shuts down, and interfacial bonding is defeated. Consequently, high rates of bioactivity (as measured by surface hydroxyapatite accretion) tend to be associated with significant local pH changes due to the release of alkali metal oxide ions.

Conventional glasses also tend to be difficult to mix to homogeneity, making quality control a problem for materials intended for implantation in the body. This is due to the relatively large grain size of the glass precursors, which generally measure approximately 10 to 1000 microns in diameter. It is difficult to obtain "molecular scale" mixing, i.e., homogeneity at the molecular level, using ordinary mixing techniques, such as stirring of the relatively viscous silicate melts.

Currently bioactive powders are limited to a $SiO_2$ content that is less than 60 mole %, which is problematic because, for example, the rate of hydroxyapatite formation is dependent upon $SiO_2$ content. Therefore, compatibility between the bioactive material and the surrounding tissue is maximized when the material's bioactivity rate (i.e., the speed at which hydroxyapatite is produced) matches the body's metabolic repair rate. However, an individual's repair rate can vary with age and disease state, among other factors, rendering identification of a single, ideal bioactivity rate impossible.

The $SiO_2$ level also determines the thermal expansion coefficient and elastic modulus of the glass. Particularly in the case of porous compositions, the ability to coat the glass onto a strong substrate (e.g., metal) significantly increases the range of clinical applications to which the glass will be amenable. Such coating is most conveniently accomplished when the thermal expansion coefficient of the glass matches that of the substrate, but restrictions on $SiO_2$ variation diminish the available range of coefficients. Particular values or ranges for the elastic modulus can also be important in certain clinical applications (such as avoiding stress shielding of the repair of long bones and joints). Consequently, some glass compositions are unsuitable if the $SiO_2$ level cannot be adjusted.

Calcium phosphate-based ceramics and glasses have the ability to bond with bone tissues and have been widely used in bone repair (Gross et al., *Ann. NY Acad. Sci.* (ed. Ducheyne and Lemons) 523 (1988); U.S. Pat. No. 6,328,990). Based on a comparison of literature data, it was suggested that 45S5 "bioactive" glass (45% $SiO_2$, 24.5% $Na_2O$, 24.5% CaO, and 6% $P_2O_5$) had the highest rate of bonding to bone (Hench, *Ann. NY Acad. Sci.* (ed. Ducheyne and Lemons) 523:54-71 (1988)). Recently, 45S5 bioactive glass has been considered for use as bioactive ceramic microspheres in 3D bone cell cultures in rotating bioreactors (Qiu et al., *Tissue Engineer* 4:19-34 (1998)). The use of bone bioactive materials is of great interest in bone synthesis in vitro because of their ability to promote cell-material bonding and the potential to enhance bone formation.

Solid bioceramic microspheres typically have a density higher than 2 $g/cm^3$. When used in bioreactors, the solid ceramic microspheres experience a high shear stress, which causes cell detachment and damage (Qiu et al., 1998). One way of solving this problem has been to reduce the apparent density of the microspheres through a hollow structure approach (Qiu et al., *Biomaterials* 20:989-1001 (1999)). Cell culture studies have confirmed that the hollow bioceramic microspheres ($SiO_2/Al_2O_3$/CaP) experience a low shear stress and can support 3D bone cell cultures in rotating bioreactors. However, because of their non-degradable component, $Al_2O_3$, hollow bioceramic microspheres cannot be completely replaced by bone tissues.

Qi et al., (*Chem. Mater.* 10:1623-1626 (1998)), described the formation of mesoporous silica spheres by a process using a cationic-nonionic surfactant mixture in aqueous acidic conditions. A typical synthesis involved stirring an aqueous acidic solution of a cationic ammonium surfactant, and a nonionic surfactant (decaethylene glycol monohexadecylether), to which an alkoxysilane was added (TEOS). The resulting material has a high surface area (1042 $m^2/g$) and ~5 µm particle size, and could be used for use as a chromatographic matrix. However, to utilize these mesoporous spheres for tissue engineering applications, they would first have to be assembled into a form that could be easily handled, and this has not been demonstrated. In addition, their bioactivity is unknown, and a long synthesis time (16 hours) would be required, making the use of such a mixture of surfactants impractical for commercial use.

Other processes have been developed for synthesizing mesoporous silica spheres in acidic solution (e.g., U.S. Pat. No. 6,334,988 (Gallis et al.), Ozin et al., *J. Mater. Chem.* 8(3):743-750 (1998)); Schacht et al., *Science* 273:768-771 (1996)) describing an emulsion process for synthesizing mesoporous silica spheres). A silicon alkoxide (TEOS) was dissolved in an organic solvent, typically mesitylene, and the mixture was slowly added to an aqueous acidic solution containing a cationic ammonium surfactant (CTAB). Schacht found that by varying the stir rate during the course of the reaction, the particle morphology could be changed. At slower stirring rates, the reaction mixture produced microspheres and some transient solid fibers; however, as the stirring rate was increased, the amount of fibers decreased with the increasing amounts of spheres. Scanning Electron Microscopy (SEM) indicated the final particles were hollow and spherical in nature. It was shown that these hollow spheres were brittle, and could be crushed with a spatula. However, the brittle nature of the spheres, in combination with the fact that they were not porous throughout their interior, were unfavorable characteristics for use as a chromatographic matrix.

The foregoing processes produce materials which exhibit regular powder X-ray diffraction patterns with one or more relatively narrow diffraction peaks, indicating that they contain a relatively ordered arrangement of pores, and are similar to SBA-3, a mesoporous material with a hexagonal arrangement of linear pores (Huo et al., *Science* 268:1324(1995)). SBA-3 is similar to the more widely known MCM-41, which has an identical arrangement of pores, but is synthesized in basic solution (Kresge et al., *Nature* 359:710-712 (1992)). While mesoporous silica having such ordered pores has use in a variety of contexts, they have not been explored for tissue engineering applications.

In an alternative process, U.S. Pat. No. 5,074,916 (Hench) teaches the use of sol-gel technology to synthesize bioactive glass powders from $SiO_2$—CaO—$P_2O_5$. The production of ceramic and glass materials by the sol-gel process has been known for many years. A "sol" is a dispersion of colloidal particles in a liquid, while a "gel" denotes an interconnected, rigid network with pores of submicrometer dimensions and polymeric chains, having an average length >1 µm. These pores are typically filled with air, so that the gel is sometimes referred to as an aerogel. Basically, the sol-gel process involves mixing of the glass precursors into a sol; casting the mixture in a mold; gelation of the mixture, whereby the colloidal particles link together to become a porous three-dimensional network; aging of the gel to increase its strength; drying the liquid from the interconnected pore network; dehydration or chemical stabilization of the pore network; and densification, to produce structures with ranges of physical properties (e.g., Hench et al., *Chem. Rev.* 90:33 (1990)). However, while such gels have nanometer-sized and mesoporous pores, they lack larger, macroscopic pores equivalent to those that exist in natural bones. Moreover, like the mesoporous silica spheres, the sol-gels tend to be brittle and mechanically weak.

Thus, a new bioactive and biodegradable composite material has, until the present invention, been needed that could be easily handled, without the brittleness and incompatibility of the prior art bone replacement materials, and that combined merits of nanopore materials (such as sol gel glass) and a fibrous construct, without the limitations of solid fibers.

Although the existing fibers in the art appear to be "transparent" to fluid, they are nonporous, and therefore lack high specific surface area because they lack a high percentage of nanopores. Accordingly, optimally such material would be characterized by a combination of nanopores for diffusion and delivery, as well as a network of bone like mesopores and macropores to enhance osteoinduction when the material is used in 3-dimensional bone tissue engineering and bone implant materials.

SUMMARY OF THE INVENTION

Provided are fibrous composites prepared by methods of the present invention comprising oxides and biodegradable polymers, in which the fibers are made of aerogel-like oxide materials having nanometer-sized pores. The fibrous composition advantageously has, at least, the following characteristics: (i) a very high surface area due to nanopores in the fibers (such pores are nevertheless large enough to permit nucleation of crystallites); (ii) an interspace between and among the fibers, constituting mesoporous/macroporous networks, ranging from several microns to several tens of microns, providing high bioactivity and a high transport rate capability for materials; (iii) macropores for tissue growth resembling that of natural bone; (iv) good mechanical properties for handling and for initial support after implant; and (v) biodegradability for implant dissolution and time-varying mechanical properties. In the field of bioactive materials, no such composition had been previously prepared, that had the combined characteristics and all of the advantages of the fibrous composition of the present invention.

Preferably, $SiO_2$ is used in the present invention because of its known bioactivity. When combined with simulated body fluid, having metal-OH groups (for example, silanol group, Si—OH) on the surface, $SiO_2$ (or silica) and other oxides have been used to induce bone-like apatite formation. But the prior art materials either lack large enough pores to grow tissue in vivo having a microstructure similar to natural bones, or they are too weak mechanically to permit useful handling or applications. On the other hand, biodegradable polymers are known, and they possess good mechanical properties. But alone, they are not bioactive.

Therefore, it is an object of the present invention to provide a bioactive, biodegradable fibrous material comprising a composite of oxides and biodegradable polymers, that can be used for tissue re-growth and regeneration and bone repair. The oxides are selected from the following, without limitation, $SiO_2$, $TiO_2$, $ZrO_2$ and $Ta_2O_5$ and other compounds that are also bioactive and capable of inducing bone-like apatite growth. The biodegradable polymers include, without limitation polylactic acid (PLA) and polyglycolic acid (PGA), poly(lactic-co-glycolic) acid (PLGA) copolymer, dextaran, collagen, poly(p-dioxanone), and poly(propylenefumarate), as well as mixtures or copolymers thereof.

Yet another object of the present invention is to provide a method for inducing bone regeneration or tissue re-growth in an animal, including human patients, by the use of the bioactive, biodegradable fibrous composition.

It is also an object to provide methods for drug or gene delivery in an animal, including human patients. The fibrous composite, therefore, for the delivery method embodiment, further comprises, without limitation a drug or therapeutic composition to be delivered from the fibrous composite. Such drug or therapeutic composition, also without limitation, native or recombinant bone morphogenic proteins or bone growth enhancing factor(s). Thus, also provided is a controlled release composition.

It is a further object of the invention to provide a method for preparing a bioactive, biodegradable fibrous composite material, comprising preparing a fibrous preform from a solid-in-oil-in-water emulsion comprising oxides and biodegradable polymers; harvesting the fibrous preform, wherein the fibers comprise gel-like oxide materials with nanometer-sized pores; exposing the fibrous preform to a solvent-based polymer solution; and removing the solvent from the resulting bioactive, biodegradable fibrous composite material. In a preferred embodiment, the fibrous preform has a silica basis. The oxides materials and polymers are as described in the composite above. The thus prepared composite is also useful for inducing bone regeneration or tissue re-growth in an animal, including human patients, as well as for drug or gene delivery in an animal, including human patients.

In addition, it is an object to provide a method for delivering a drug or therapeutic composition in an animal, comprising administering the bioactive, biodegradable fibrous composite material to an animal at the site needed. Included in this method is the delivery of native or recombinant bone morphogenic proteins or bone growth enhancing factor(s). Also included are fibrous composites prepared by the foregoing methods.

An additional object of the present invention is to provide a method for producing bioactive and degradable scaffolds for 3-dimensional bone tissue engineering.

Additional objects, advantages and novel features of the invention will be set forth in part in the description, examples and figures which follow, all of which are intended to be for illustrative purposes only, and not intended in any way to limit the invention, and in part will become apparent to those skilled in the art on examination of the following, or may be learned by practice of the invention.

BRIEF DESCRIPTION OF THE FIGURES

The foregoing summary, as well as the following detailed description of the invention, will be better understood when read in conjunction with the appended figures.

FIG. 6A shows the fracture surface at 20 μm and FIG. 6B shows the exterior surface at 10 μm.

DESCRIPTION OF PREFERRED EMBODIMENTS OF THE INVENTION

Figure 1:
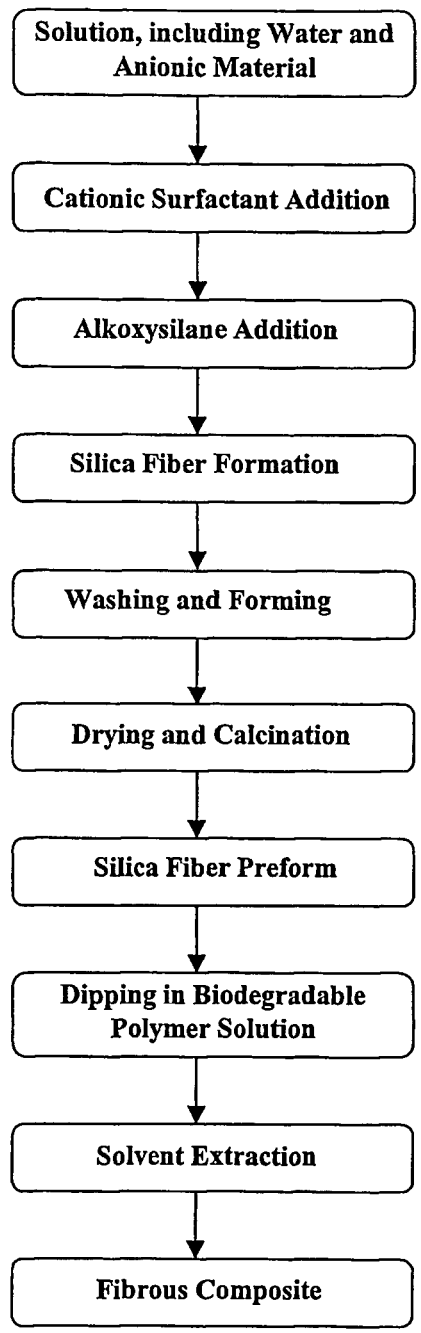
FIG. 1 is a flow chart delineating a method of preparing fibrous composites.

The present invention provides fibrous composite materials, as well as the preparation and use therefor, comprising oxides and biodegradable polymers, in which the fibers are made of aerogel-like oxide materials with nanometer-sized pores. The fibers are preferably hollow, to further increase the surface area and lower the density of the composite material, thus meeting the need for an osteogenic composite material for tissue engineering, such as for tissue re-growth, bone implants, and bone repair, that is bioactive (i.e., can bond to living tissue, such as bone) and resorbable or degradable (i.e., can be replaced by tissue after a period of implantation). In addition to acting as an implant material, such composites are also useful as drug or gene delivery devices, e.g., for tissue regeneration. The fibrous composite, with or without biodegradable polymers, has been found to induce bone-like apatite formation at body temperature in fluids equivalent to those in the human body.

The present fibrous composites have shown good mechanical strength and can be easily handled. When immersed in simulated body fluid, they induce bone-like apatite growth. They can be easily applied to a surface or substrate, in the form of, for example, patches or coatings, to aid tissue re-growth in the body. They can also be easily formed into shaped objects of a desirable shape and size to aid in the bone repair and replacement process. Because the fibrous nature of the composite material adds a degree of flexibility to the preferred embodiments of the present invention, the mechanical handling capability of the final product is actually a significant improvement over the prior art, since it is not as brittle as bulk pieces that are presently used for tissue regeneration purposes.

Silica ($SiO_2$) and other oxides, such as $TiO_2$, $ZrO_2$ and $Ta_2O_5$ are bioactive and can induce bone-like apatite growth due to the action of silanol (Si—OH) and similar metal-OH groups, which form on oxide surfaces. For example, silanol (Si—OH) groups nucleate a bone-like apatite layer, which grows by utilizing the calcium and phosphate ions from the body fluid. Therefore, $SiO_2$ and its composites can be used as a scaffold for bone growth.

It is well recognized that the presence of high surface area is advantageous in a porous bioactive material. In the present invention, a high specific surface area (per gram, or per volume) is desirable because bioactivity is a surface phenomenon. Accordingly, without sacrificing other characteristics, such as mechanical strength, the higher the surface area the better for a bioactive, biodegradable, osteogenic composite material for tissue engineering, or drug delivery purposes. Thus, the fibrous composite material of the present invention is advantageous because it has a very high surface area.

Gels and glasses can be used for bone-like apatite formation, but in monolithic form they lack a microstructure similar to natural bones, so the tissue growth is limited to the surface of the monolith and little ingrowth can occur. In addition, their mechanical properties are too weak for handling in many applications.

Dental implants (usually of titanium with or without hydroxyapatite coating) are used as surrogates of tooth roots after implantation in edentulous jaws. Nevertheless, titanium is not bioresorbable. When used for bone replacement, its superior strength eventually causes the degradation of natural bone that suffers from a reduced load-bearing need. As a result, porous biomaterial implants and solid prosthetic implants are often preferred for orthopedic, craniofacial and dental applications, wherein there is a need to integrate the implant with the viable bone of the patient for successful osteointegration, excluding of course, failures attributable to implant micromotion and infection.

The fibrous composites prepared by the present invention have mesopores that provide high bioactivity, and macropores for tissue growth that resembles natural bones, good mechanical properties for handling and for initial support after implant. They also provide biodegradability, permitting implant dissolution and time-varying mechanical properties. In a preferred embodiment, the porous osteoconductive bioactive fibrous composition is used to restore bone defects by insertion at the site of the bone defect or as an implant. In some instances, treatment requires the insertion of solid prostheses to substitute for a part of the skeleton, for example, as is commonly done for femoral or knee replacement (e.g., hip or knee prosthesis). The fibrous composite can be formed into specific shapes or block composite forms by centrifugation.

The bioactive fibrous composition of the present invention may take the form of a manufactured article, or the form of a biomaterial having a unique porous configuration, for use in particular embodiments of the article. In either case it is preferred that the composite be capable of inducing the spontaneous initiation of bone formation, even if not in direct contact with viable bone.

Although fibrous mesoporous composites of oxides and polymers have been previously synthesized (see e.g., Stucky et al., 1996), and it has been proposed that such materials may be potentially relevant to biomineralization in living organism, they have not been explored for tissue engineering applications. In the case of oxides, they also do not contain polymers. Therefore, these fibrous mesoporous composites are relatively brittle and difficult to handle.

By comparison, the fibrous composites of the present invention comprise biocompatible oxides and polymers, in which the fibers are per se made of gel-like oxide materials with nanometer-sized pores, and the polymers are biodegradable. The fibers are preferably hollow, to further increase the surface area and lower the density of the composite material. The polymers form bonding and linkage at the intersections of fibers.

For the purpose of a porous biomaterial implant using an osteoinductive, bioactive fibrous composition of the present invention, there is provided a method of preparing a biomaterial which can be used for at least part of a bone implant to be implanted into a patient at a site where bone growth is required. The method includes preparing the biomaterial with an interconnected porous configuration, which includes hollow-cored fibers delineating interconnecting porous spaces having such shapes and dimensions as impart to the biomaterial the ability to induce or enhance the rate and/or amount of bone growth at the site. The hierarchical pore structures within the present composite range from nanopores within the fibers, to mesopores in the inner cores of the fibers, to the larger macropores between the fibers and the linkage polymers.

The preferred fibers contain nanopores at a concentration ranging from approximately 45-75%. More preferably the fibers contain at least 50-70% nanopores, still more preferably 55-65%, and even more preferably at least about 60% nanopores or more.

The nanopores in the fibers range in size from not less than about 1.5 nm, up to about 10 nm in width, preferably from 2.0 to 5 nm, and more preferably in the range of 2.0 to 3 nm. Small pore size increases a specific surface area (surface area per gram or per volume), given the same total pore volume (or porosity). Mathematically, specific surface area is a reciprocal of pore diameter, i.e., specific surface area scales inversely as pore size. Therefore, smaller, nanometer-sized pores are preferred. However, there is a lower limit of pore size, at about 1.5 to 2 nm, below which ion diffusion and hydroxyapatite nucleation appears to be restricted. Consequently, the fibrous composite material of the present invention relies upon pore size of the porous fibers to be as close to this lower limit as possible, with the majority of the nanopores in the range of 2-10 nm (i.e., larger than about 1.5 to 2.0 nm) to maximize the available surface area of the composite, without limiting ion diffusion and hydroxyapatite nucleation. Thus, the enhanced compositional range of bioactivity obtainable with the present invention derives from the presence of small pores (approximately 2.0 to 10 nm) in the fibers, combined with the resulting large surface area.

Sol gel glasses have pore sizes in the 2-10 nm ranges, and hence comparable specific surface area, which is why they have been proposed for bioactive applications in the past. However, fluids and/or nutrients cannot flow into such material easily, because the flow channels are similar in size to the pore size, and thus are too small. Therefore, in use only the surface of a sol gel glass body becomes "wet," while the interior remains "dry." As a result, very long soaking time is needed to wet the entire piece, which obviously contradicts the purpose of creating a natural bone equivalent.

On the other hand, fibrous composite of the present invention has large pore spaces between the fibers, which allow fluids to immediately flow into, and fill the space. Thus, the entire fibrous composite can be thoroughly and instantaneously soaked (e.g. with the polymer solution or with the simulated body fluid, and the resulting fibrous microstructure looks similar to bones on the micron scale. Therefore, the fibrous construct for the composite material is particularly attractive.

"Pore size" as referred to herein, refers to the dimension of fiber diameter, which is generally several microns, and should be classified as mesopores or even macropores. The fibers typically range from about 2 to 20 micrometers in cross-sectional diameter, more preferably from about 5 to 15 micrometers, and even more preferably from about 5-10 micrometers. The average interfiber pore size may range from 0.5× to 10× of fiber diameter. The fiber loading, that is the volume occupied by the fiber within the space, ranges from about 5% to 40% of the volume, preferably in the range of 10% to 30%, and more preferably in the range of about 20% to 30%. The hollow core of the fiber may have an internal diameter of from about 50% to 90% of the fiber diameter, preferably 55% to 85%, and more preferably from about 60% to 80% of the fiber diameter.

Thus, the fibrous composite material of the present invention is useful as both an implant material in 3-dimensional tissue engineering and as a microcarrier, depending on the condition to be treated in an animal, including a human patient. In certain embodiments the utilities are combined and the fibrous composition is formed into an osteoinductive implant material or implant coating material to which certain growth enhancing polymers have been added, such as growth factors, for the controlled release of the, e.g., growth factors during the osteoinductive healing process after the implant has been placed in the body.

It is further known that a mesoscopic fibrous structure, missing in many of the prior art osteoconductive materials, such as in dense bioglass, is advantageous for tissue growth and bone repair. Thus, the present fibrous composition is particularly useful because it has a relatively high surface area, mostly provided by the aerogel-like fibers, yet it also contains mesopores and an open-connected fibrous microstructure that resemble the microstructure of natural bone. These ultrastructural features, particularly in the preferred silica gel, give rise to a large area density of nucleation sites for hydroxyapatite crystallites. With this favorable deposition environment, buildup of a hydroxyapatite layer can take place at higher rates and throughout the fibrous composites, over their entire thickness of the material without limit, thus allowing complete bone inter-growth, which enhances the strength of the re-grown structure. It is also possible that growth may proceed with lower proportional concentrations of CaO and $P_2O_5$ than would be necessary for ordinary bioactive glass compositions. Consequently, bioactive materials can be prepared with relatively large levels (100%) of $SiO_2$ that exhibit relatively small local pH variations in vivo.

Polymers incorporated into the present fibrous composites are desirable because they improve the mechanical properties of the final material, making them easy to handle, and they allow adjustment of resorption or biodegradability of the final product. Such polymers may be either synthetic, such as poly(lactic acid), or natural, such as collagen. Moreover, it is advantageous to use a silica gel and certain polymers that degrade over time, having the additional advantage of resorption into the body of the host patient, eventually removing the man-made structure from the body. The resorptive capability of the present fibrous composite, when combined with a selected composition, is also a characteristic that is useful for the controlled, delayed release of bioactive agents (meaning drugs, growth hormones, vitamins, extracts, demineralized bone matrix or BMP compounds, dyes, genes or other medicinal or therapeutic substances and the like, from natural or recombinant sources) into the body.

The invention extends to a method of inducing and enhancing the rate and amount of bone growth in a patient, in a site where bone growth is desired, which includes selecting or preparing a porous biomaterial implant of having present fibrous composite material, having an appropriate overall shape and size for accommodation at the site of a bone defect, and comprising a porous framework wherein, preferably hollow-cored fibers delineate interconnecting porous spaces, and placing the porous biomaterial implant in the patient at the site of a bone defect where bone formation and growth is required. For the purpose of the solid implant with osteoinductive configurations for dental, craniofacial and orthopedic applications, according to the invention, there is provided a solid implant for implantation into a patient at a site where bone replacement is required, said implant comprising a body formed from or coated with the present composite material comprising hollow-cored fibers delineating interconnecting porous spaces.

The mesoporous fibers in the present technology are prepared by an emulsion process using highly acidic conditions. Source materials contain halide ions, cationic surfactant and alkoxysilane in the case when silica is desired as the fiber constituent. (In alternative embodiments other fibers, e.g., $TiO_2$, $ZrO_2$ use source materials other than alkoxysilane, see e.g., materials used by Schacht et al., 1996). When alkoxysilane (from 3 to 5° C.) is used, it provides the source of positively charged inorganic species of silica under highly acidic conditions. Halide ions are preferably bromides and/or chlorides. Surfactants control the interaction between these charged inorganic species. Preferred surfactants are for example, without intended limitation, cationic surfactants, such as CTAB (cetyltrimethylammonium bromide), CTAC (cetyltrimethyl ammonium chloride), DTAB (dodecyltrinmethylammonium bromide), and DTAC (dodecyltrimethylammonium chloride). Neither catalysts, nor exogenous energy sources, such as heat, microwave or irradiation have been used in this process, but either could be used in combination with alternative embodiments of the methods of the present invention to enhance the intended formulation or rate of reaction to form the fibers.

Previous investigations of bioactive glass compositions that bond to bone demonstrate that bonding occurs within 10 to 30 days if the surface area developed in simulated test solutions falls within the range of at least 200-500 $m^2/g$; see, e.g., U.S. Pat. No. 4,171,544. Accordingly, fibrous compositions of the present invention all exhibit surface areas several times greater than 200 m$^2$/g.

Using silica as an example, the silica fibers obtained by this technology have a typical surface area above 1000 m$^2$/g. The pore volume exceeds 0.70 cc/g and the pore size is 2.0-5.0 nm, preferably 2.0-3.5 nm, more preferably 2.0-3.0 nm. In an exemplified embodiment the pore size was 2.4 nm. The fibers have a hollow structure inside (hollow cores), and they are mesoscopically dispersed in the porous silica composite. Essentially, the fibers are tubes with porous walls. In fact, from 25% to 90% of the fibers of the present invention are hollow, more preferably 40% to 60% of the fibers are hollow, still more preferably, at least 40% of the fibers are hollow, and even more preferably at least 50% of the fibers are hollow. In a preferred embodiment, more than 70% of the fibers are hollow. Thus, the hollow core of the fiber advantageously provides substantially greater pore space and surface area to the embodied material than would be possible using solid or dense fibers.

In preferred embodiments of the invention, biodegradable polymers, such as polylactic acid (PLA) and polyglycolic acid (PGA) or combinations or copolymers thereof, can be used for the composites. In addition, polymers, such as, but without limitation, dextaran, collagen, poly(p-dioxanone), and poly(propylenefumarate), or combinations of any of the foregoing, may be used in preparing the fibrous composites of the present invention. These polymers are preferred because they have already received approval for use by the US Food and Drug Administration (FDA). PLA has a much slower degradation rate than PGA. Therefore, biodegradability can be controlled by adjusting the composition of poly(lactic-co-glycolic) acid (PLGA) copolymer, ranging from a few weeks to over one year.

To impregnate the fibrous composite with the selected polymer contact absorption is preferred. The composite material is preferably dipped into an organic solvent, such as acetone, containing biodegradable polymers at a concentration of about 0.01% to 2%, but optimally at about 0.5%. After that, the solvent is removed, typically in vacua. The impregnation process can be repeated 1, 2, or 3 or more times to increase the amount of polymer in the fibrous composite material. Typically, it is repeated 2-3 times. However, if the polymer concentration in the feed solution is too high (i.e., exceding the foregoing stated ranges), it is possible to fully cover the fibers and choke off the meso/nano pores. On the other hand, if polymer simply grafts to the surface of fibers, then this choking is less likely to happen, unless the polymer concentration is very high.

After dipping the fiber preform into the polymer solution, preferably for 2 to 3 minutes or less (i.e., essentially soaking for the 2-3 minutes or shorter), but not more than 5-10 minutes on average, the polymers form a coating at the intersections of fibers. After a period of immersion in simulated physiological solution for 3 days to 4 weeks, more often from 3 days to 2 weeks, but preferably for about 1 week, microspheres were fully covered by a calcified layer that consisted of 2 to 3 μm globules. Calcium and phosphate were detected on the calcified surface within the fibrous composite material by SEM. X-ray diffraction (XRD) analysis of the composite cross-section further confirmed the apatite formation on the silica surfaces, although Fourier transform infrared spectroscopy could in the alternative be used to visualize crystalline calcium hydroxyapatite, as indicated by the presence of orthophosphate bands (P—O at 560, 606, 950 and 1044 cm$^{-1}$) and C—O bands (C—O at 1410 and 874 cm$^{-1}$).

However, as proven by SEM scanning, the polymers do not block most of the open pore space between fibers, the hollow cores of fibers, or the nanopore space within fibers, i.e., not more than 3-10% of the open pore space, preferably not more than 5% of the open pore space is blocked. Therefore, by 'most' is meant at least 90%, and preferably more than 95% to 97% of the open pore space remains unblocked, even after polymer treatment.

The biodegradable polymers provide time-varying mechanical properties. This is advantageous in bone repair or replacement, since it provides higher strength in the initial phase (when first introduced into the body) before bone growth has begun. Then the polymer strength decreases with time, so that the implant does not overtake the strength carrying ability of the neighboring healthy bones in the host patient. Otherwise, the patient's surrounding healthy bones may lose density and deteriorate over time. The fibrous material can also be mixed with a liquid to form a coating material.

The bioactive fibrous composition can be modified in a number of ways. For example, the hydrophilic or hydrophobic nature of the composite may be altered by the addition of carbohydrates or lipids. The addition of acidic phospholipids to the composite enhances its calcium binding capacity. Additional macromolecules may be added to the composite to achieve a particular biological response, such as collagen to enhance the growth of hydroxyapatite. In addition, calcium hydroxide in soluble form or as part of a protein-based particle may be added to increase the pH of the composite.

Moreover, cross-linking agents or polymers (such as collagen) may be added to the fibrous composition, or subjected to the entire composite to increase the strength, to further retard its degradation, and to decrease its solubility. The degree of composite degradation and its inflammatory response may also be controlled by the stabilizing affect of alkaline phosphatase or other proteinaceous materials.

To predict bone-bonding capability of the fibrous composition, the material was soaked in simulated body fluid (SBF) to induce the formation of apatite, the appearance of which thereby confirms that bone bonding would occur in vivo. This applies a technique first proposed by Radin and Ducheyne in *J. Biomed. Mater. Res.* 27:35-45 (1993), and later exemplified in U.S. Pat. No. 6,328,990 (each of which are herein incorporated by reference). They proposed immersion in a simulated physiological solution comprising a 0.05 M Tris buffer (pH 7.3) supplemented with plasma electrolytes at 37° C. In the reported process, the immersed particles were shaken, and incubated from 1 hour to 3 days. The SBF was changed every 2 hours for the first 6 hours and then changed at 24, 48 and 72 hours. Notably, however, in the present invention the immersed composite is not intentionally shaken.

Fourier transform infrared spectroscopy (FTIR) is also available, and can be used in the present invention to examine the spectra of the material after immersion, thus following the formation of hydroxyapatite over a course of hours and/or days. After immersion in simulated physiological solution for 6 hours, amorphous calcium phosphate was formed in the reported composition, as indicated by the presence of a bending vibration mode of the PO$_4$ groups (P—O bend). (Notably, the apatite coating is used for evaluation purposes; it is not added prior to implanting the composite). After immersion for 1 day, the P—O bend peak divided, indicating the presence of crystalline calcium phosphate ceramic phase. The appearance of bands located at 870 cm$^{-1}$ (C—O bonds) and 960 cm$^{-1}$. P—O symmetric stretch, characteristic of hydroxyapatite, indicated that the crystalline phase was carbonated calcium hydroxyapatite. In the reported material, the pH increased with time, but this was not measured in the present fibrous composite.

In testing the preferred embodiments of the present invention, the apatite coverage is uniform and complete, penetrating the pore space between fibers, as demonstrated by light microscopy and scanning electron microscopy (SEM) analyses. These results demonstrated the successful production of bioactive and biodegradable composite material for use in tissue engineering and regeneration. The composite material has an advantage over prior art composites in terms of the bioactivity conferred by the use of the fibrous network and the biodegradability conferred by use of both the polyester polymer and the fibrous oxide-based gel. Hydroxyapatite and other calcium phosphates that had been used before could not be resorbed. Size of the composite fibers and porous network was controlled with this method, offering another advantage over previous methods. Because the degradation product of silanol or the other selected metal oxides can be metabolized by the body, the present fibrous composite makes an excellent implant material and an excellent carrier providing reservoirs for controlled delivery of a wide range of bioactive agents in animals, including humans. The selected physical characteristics of the bioactive fibrous composition can regulate the rate of release of the materials being delivered from the composite.

In the present embodiments of the invention, the use of simulated physiological fluid as a way to predict bone-bonding ability of implanted materials effectively demonstrated that the composite material of the present invention has the ability to bond with tissue and confirms that bone bonding would occur in vivo. The successful acquisition of calcium hydroxyapatite over the complete surface of the composite material confirms that it will provide a support for new bone formation and link the bone or tissue with the implant.

For applying a coating of a fibrous biomaterial to an implant comprising the fibrous material, to aid osteointegration, a number of physical and chemical techniques are available. These include, but are not limited to: biological deposition from simulated body fluid; adhesively bonding hydroxyapatite (HA) to the substrate; radiofrequency sputtering; pulsed laser deposition; hot isostatic pressing (HIPPING); reactive physical vapor deposition; slurry coating; electrophoretic deposition and sintering; high velocity flame spraying; ion beam sputter deposition; or magnetron sputtering. Although if another implant material (for example, a base made of a metal, such as titanium), is coated with the fibrous composite material of the present invention, high heat coating methods are not effective.

Furthermore, after coating, a number of post-treatments can be carried out, for example, radiofrequency glow discharge treatment; vacuum heat treatment; ion implantation; and sterilization treaments, such as gamma ray irradiation, autoclaving, and the like.

By varying the amount of $SiO_2$, it is possible to substantially match the thermal expansion coefficients of the bioactive fibrous compositions with those of compatible substrates, although thermal stress is not a problem for the flexible, fibrous material, in the way it is a problem for monoliths. The thermal expansion coefficients associated with the compositions of the present invention vary with the ratio of $SiO_2$ to CaO plus $P_2O_5$ (i.e., $SiO_2/(CaO+P_2O_5)$), in which the amount of CaO and $P_2O_5$ can be calculated from the apatite coverage.

In an alternative embodiment, a portion of the composite-forming material comprises the active ingredient held within the network of pores, and a portion is held within the polymerized particles forming the network.

In a preferred embodiment, the bioactive fibrous compositions of the present invention can advantageously be cast into defined shapes with good registration of surface detail. Due to their structure, there is much greater uniformity in these compositions than is found in allogenic tissue. Furthermore, a significant advantage of the present invention is the ability of the fibrous compositions to be shaped by centrifugation, followed by detail trimming and cutting to precise size by conventional means, thereby avoiding the risk of gross breakdown of the entire composite matrix or the development of severe surface defects as may occur in ground or milled products. This finding is significant since diagnostic techniques now allow the accurate three-dimensional representation of bony defects with the resultant preparation of a graft or implant via CAD/CAM technology. Thus, the fibrous composite can be prepared to precise specifications for insertion as an osteogenic graft material in a bony defect.

The reactivity of the composite material was explored in more detail by examining the formation of the mineral layer on the surface of the fibers following the in vitro immersion method (in simulated physiological solution). Changes in concentrations of calcium (Ca), phosphate ($PO_4$) and silicon (Si) in the immersion solutions as a function of incubation time may also be analyzed using standard wet chemical methods.

The present invention is further described by example. These examples are provided for purposes of illustration only, and are not intended to be limiting unless otherwise specified. The various scenarios are relevant for many practical situations, and are intended to be merely exemplary to those skilled in the art. These examples are not to be construed as limiting the scope of the appended claims; rather such claims should be construed to encompass any and all variations that become evident as a result of the teachings provided herein.

EXAMPLES

Example 1

Method of Preparing and Testing Fibrous Silica/Polymer Composites

A flow chart of the method of preparing bioactive fibrous composites is shown in FIG. 1, wherein the fibers are silica. 1. 0.6973 g of cetyltrimethylammonim bromide (CTAB) surfactant and 22.2115 g of HCl (37.3 wt %) were added to 126.0734 g $H_2O$. CTAB and HCl are used as cationic surfactant and anionic material to allow emulsion formation of two phases (oil and water). After emulsification, terabutylorthosilicate (TBOS) as silicon source is added dropwise to the solution. The solution is held at room temperature for 5 to 7 days to allow reaction without stirring. The reacted solution is then washed 5 times with centrifuge. After centrifuging at 10,000 rpm for 2 minutes, it is dried at room temperature to harvest the fibers. The fibers are heated at 1° C./minute to a temperature of 500° C., and held at that temperature for 8 hours for calcination.

Figure 2:
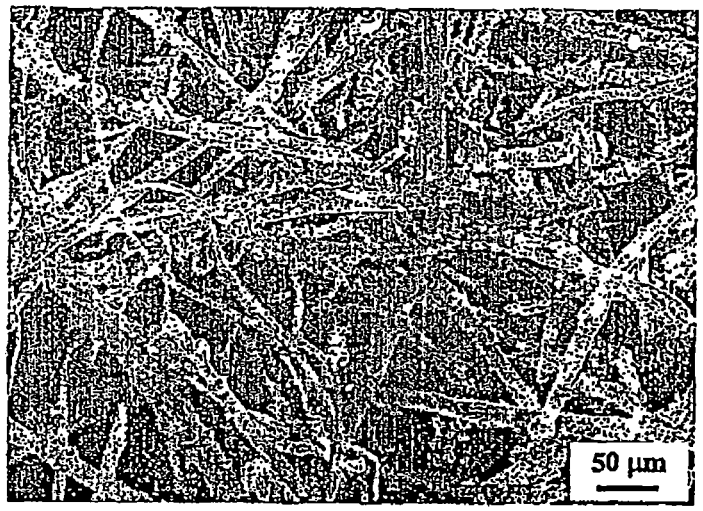
FIGS. 2A and 2B depict SEM micrographs of a fiber preform at 50 μm (FIG. 2A) and at 5 μm (FIG. 2B) showing their arrangement and hollow fiber cores.
Figure 2:
Figure 3:
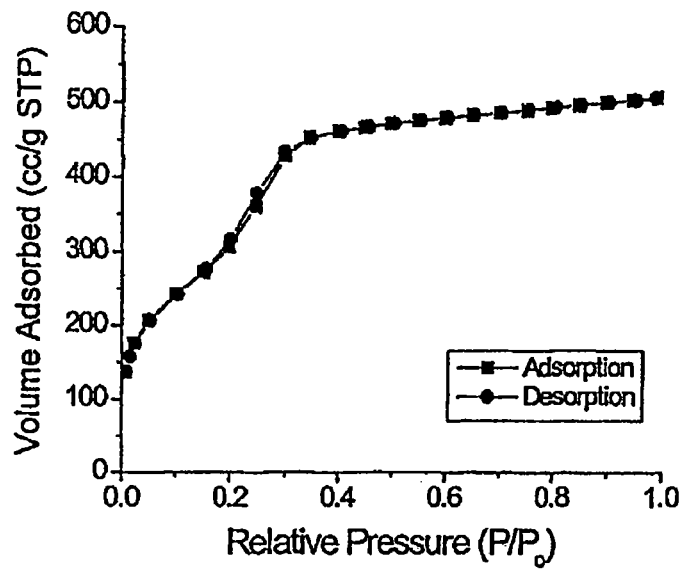
FIGS. 3A and 3B reveal the pore structure of mesosilica fiber composite by FIG. 3A nitrogen sorption isotherm, by FIG. 3B BJH pore size distribution.
Figure 3:
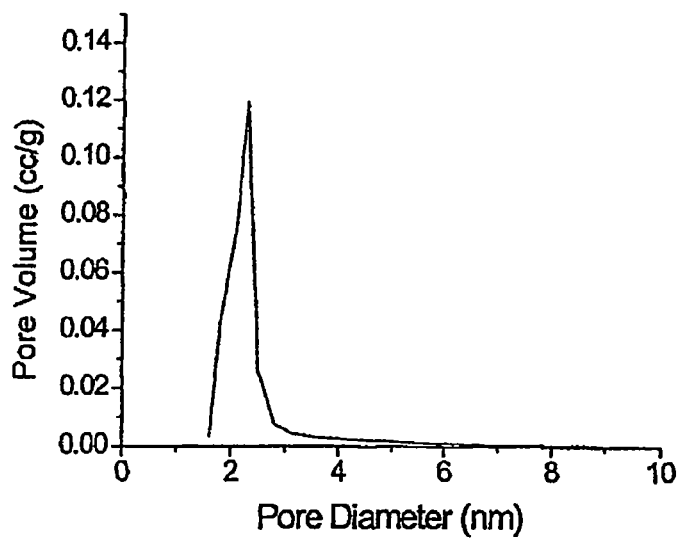

The prepared fibers were observed with scanning electron microscope (SEM). A typical microstructure is shown in FIG. 2, which show the core. The pore structure of the fibers can be probed by Brunauer-Emmett-Teller (BET) and Barrett-Joyner-Halenda (BJH) methods as shown in FIG. 3. These fibers have a BET surface area of 1280 $m^2/g$. The pore volume was 0.78 cc/g and the average pore diameter was 2.4 nm.

Figure 4:
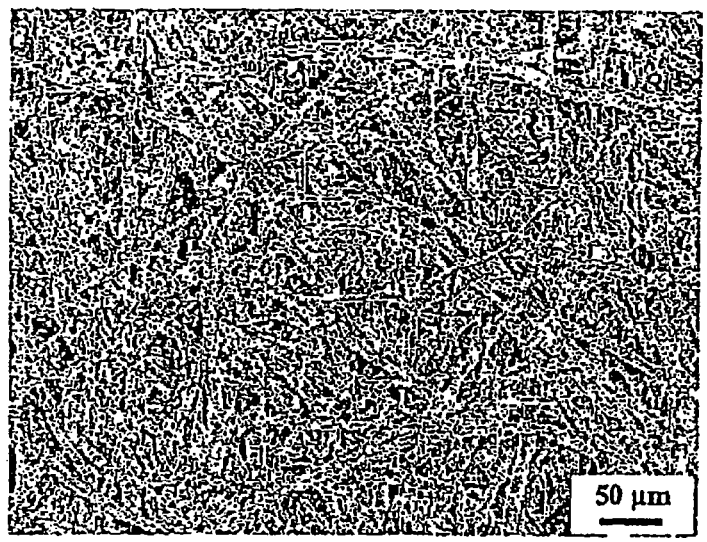
FIGS. 4A and 4B depict SEM micrographs of a fibrous silica/polymer composite at 50 μm (FIG. 4A) and at 5 μm (FIG. 4B). A lip of polymer is seen in the center left.
Figure 4:
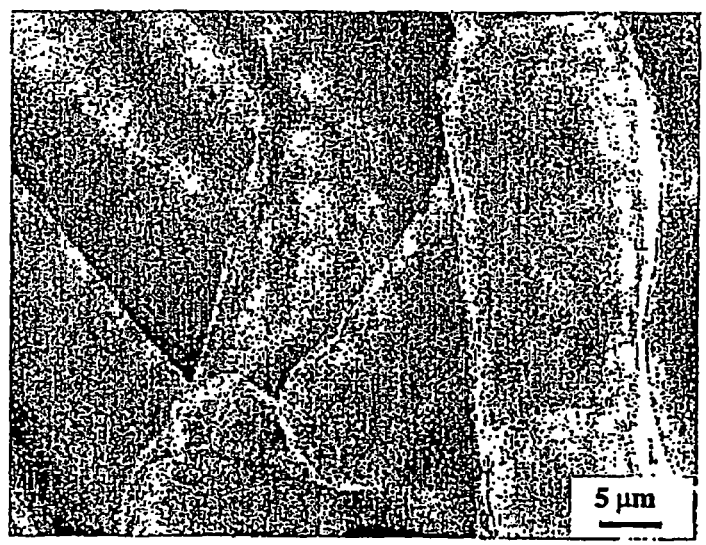

A polymer solution was prepared by dissolving 0.5 g PLGA (poly(lactic-co-glycolic) acid copolymer) in 50 g acetone. The silica fibrous preform was dipped in the solution and withdrawn. This dipping process is repeated several times, if necessary. After dipping, acetone is removed by holding the sample in vacuum. The preparation of the final fibrous silica/polymer composite was then completed. A typical SEM microstructure is shown in FIG. 4. When compared with FIG. 2, lips of polymer can be seen around the intersections of fibers. The composite handles very easily because of the added mechanical strength due to polymer impregnation.

The fibrous composite is soaked in simulated body fluid (SBF). SBF was prepared by dissolving NaCl, $Na_2SO_4$, KCl, $MgCl_2.6H_2O$, $CaCl_2.2H_2O$, $KHPO_4$ and $NaHCO_3$ in water. Ion concentration of SBF is listed in Table 1.

TABLE 1

Ion concentration in simulated body fluid (mM).

| $Na^+$ | $K^+$ | $Mg^{2+}$ | $Ca^{2+}$ | $Cl^-$ | $HCO^{3-}$ | $HPO_4^{2-}$ | $SO_4^{2-}$ |
|---|---|---|---|---|---|---|---|
| 142 | 5 | 1.5 | 2.5 | 147.8 | 4.2 | 1.0 | 0.5 |

Figure 5:
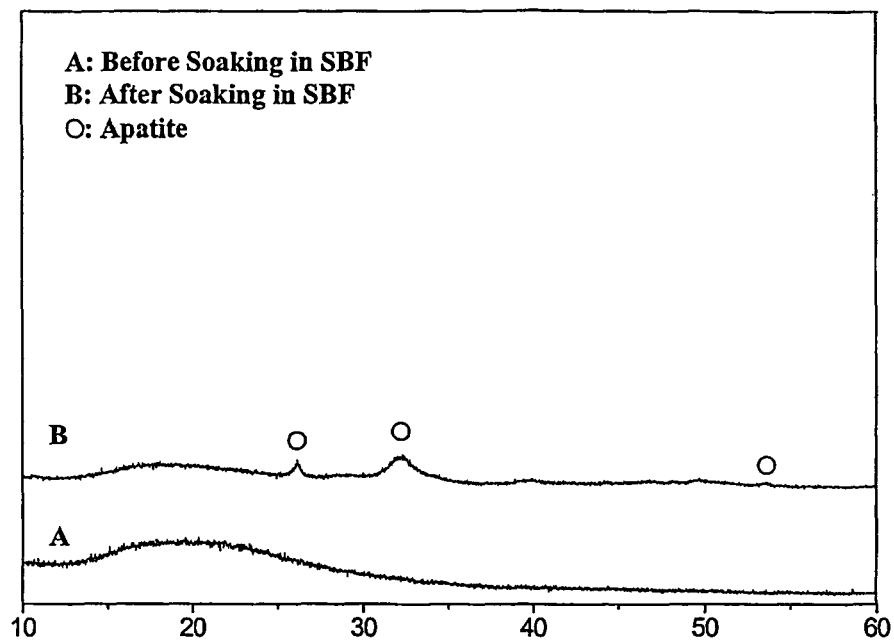
FIG. 5 graphically shows a comparative X-ray diffraction pattern, wherein the formation of apatite on the silica surface is shown by line (A) before soaking in simulated body fluid (SBF), and line (B) shows the effect after soaking.
Figure 6:
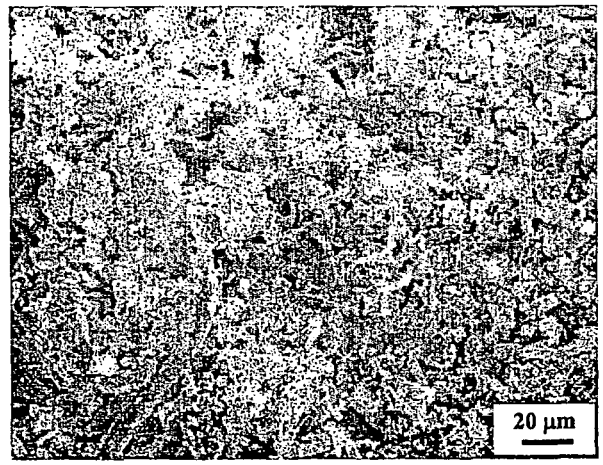
FIGS. 6A and 6B depict SEM micrographs of a fibrous silica/polymer composite after soaking in SBF.
Figure 6:
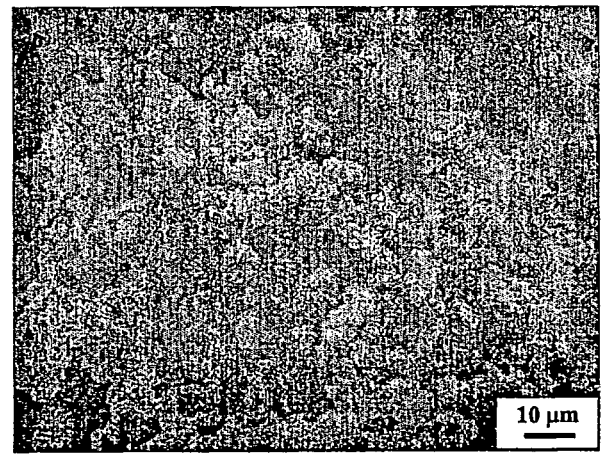

The solution was buffered at 7.4, using HCl and tris(hydroxymethyl)aminomethane, and held at 36.5° C. (~body temperature). After 1 week, apatite on the silica surface is formed, as observed with SEM and X-ray diffraction (XRD). A typical diffraction pattern is shown in FIG. 5, which illustrates the peaks that are characteristic of apatite. Several SEM micrographs are shown in FIG. 6 to illustrate the general distribution of apatite, and the remnant of fibers. The thus prepared fibrous composite is ready for applications in tissue engineering for the repair, reconstruction, and replacement of bone, and/or for applications involving drug and gene delivery by incorporating active biomolecules. It may also be used as a biosensor by incorporating sensing molecules, or as a bioreactor by incorporating enzymes.

The disclosures of each patent, patent application and publication cited or described in this document are hereby incorporated herein by reference, in their entirety.

While the foregoing specification has been described with regard to certain preferred embodiments, and many details have been set forth for the purpose of illustration, it will be apparent to those skilled in the art without departing from the spirit and scope of the invention, that the invention may be subject to various modifications and additional embodiments, and that certain of the details described herein can be varied considerably without departing from the basic principles of the invention. Such modifications and additional embodiments are also intended to fall within the scope of the appended claims.

What is claimed is:

1. A bioactive, biodegradable, resorbable fibrous composite of bioactive, gel-like silica or metal oxide materials and biodegradable polymers, the fibrous composite comprising: a plurality of fibers, comprising not less than 25% hollow-core fibers, assembled into a sizable fibrous preform comprising pores in a conductive interconnecting-porous configuration, wherein (i) nanopores ranging in size from 1.5 to 10 nm in diameter are in and on the interconnected fibers and inner cores of the hollow fibers; and wherein the resulting fibrous composite has an overall surface area of greater than 1000 $m^2/g$; and (ii) mesopores and macropores are interspaced between and among the interconnecting fibers of the porous configuration, wherein interfiber pore size ranges from 0.5 to 10 times fiber diameter providing fluid transport in <10 minutes.

2. The fibrous composite of claim 1, wherein the oxides are selected from the group consisting of $SiO_2$, $TiO_2$, $ZrO_2$ and $Ta_2O_5$.

3. The fibrous composite of claim 2, wherein silanol (SiOH) and similar metal-OH groups form on the oxide surfaces.

4. The fibrous composite of claim 1, wherein the biodegradable polymers are selected from the group consisting of polylactic acid (PLA), polyglycolic acid (PGA), poly(lactic-co-glycolic) acid (PLGA) copolymer, dextaran, collagen, poly(p-dioxanone), and poly(propylenefumarate), as well as mixtures thereof, and co-polymers thereof.

5. The fibrous composite of claim 1, further comprising a bioactive agent or therapeutic composition.

6. The fibrous composite of claim 5, wherein the bioactive agent comprises bone morphogenic protein, bone growth enhancing factors, drug, growth hormone, vitamin, extract, demineralized bone matrix, dye, genetic material, or combinations thereof, from natural or recombinant sources.

7. The fibrous composite of claim 1, wherein the fibers are porous, and wherein at least 30% of the porous fibers are hollow.

8. The fibrous composite of claim 7, wherein at least 50% of the porous fibers are hollow.

9. A bioactive, biodegradable, controlled-release delivery system comprising the fibrous composite of claim 1 and a bioactive agent or therapeutic composition incorporated therein for release from the system upon degradation of the biodegradable fibrous composite.

10. A method for delivering a bioactive agent or therapeutic composition in or to an animal using the fibrous composite of claim 1, comprising:
incorporating the bioactive agent or therapeutic composition within the fibrous composite; and
administering to the animal the fibrous composite and the bioactive agent or therapeutic composition incorporated therein.

11. The method of claim 10, wherein the animal is a human.

12. The method of claim 10, wherein the bioactive agent comprises a drug, growth hormone, bone growth enhancing factor, vitamin, extract, demineralized bone matrix, bone morphogenic protein, dye, or genetic material, or combinations thereof, from natural or recombinant sources.

13. A method for delivering a bioactive agent or therapeutic composition in or to an animal using the delivery system of claim 9, comprising:
administering to the animal the fibrous composite and the bioactive agent or therapeutic composition incorporated therein; and
effecting release in the animal of the incorporated bioactive agent or therapeutic composition upon degradation of the biodegradable fibrous composite.

14. The method of claim 13, wherein the animal is a human.

15. The delivery system of claim 9, wherein the bioactive agent comprises a drug, growth hormone, bone growth enhancing factor, vitamin, extract, demineralized bone matrix, bone morphogenic protein, dye, or genetic material, or combinations thereof, from natural or recombinant sources.

* * * * *

UNITED STATES PATENT AND TRADEMARK OFFICE
CERTIFICATE OF CORRECTION

| | |
|---|---|
| PATENT NO. | : 8,580,291 B2 |
| APPLICATION NO. | : 10/507059 |
| DATED | : November 12, 2013 |
| INVENTOR(S) | : Hoon Choi et al. |

It is certified that error appears in the above-identified patent and that said Letters Patent is hereby corrected as shown below:

In the Specification

Column 1,
Lines 12-15, delete "This invention was supported in part by U.S. National Science Foundation, Grant Number DMR00-79909. Accordingly, the Government may have certain rights in this invention." and insert -- This invention was made with government support under DMR0079909 awarded by the National Science Foundation. The government has certain rights in the invention. --

Signed and Sealed this
Sixteenth Day of May, 2023

Katherine Kelly Vidal
*Director of the United States Patent and Trademark Office*